(12) United States Patent
Liu

(10) Patent No.: US 9,675,113 B2
(45) Date of Patent: Jun. 13, 2017

(54) ELECTRONIC CIGARETTE

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 731 days.

(21) Appl. No.: 14/062,551

(22) Filed: Oct. 24, 2013

(65) Prior Publication Data

US 2015/0053216 A1 Feb. 26, 2015

(30) Foreign Application Priority Data

Aug. 26, 2013 (CN) .................... 2013 2 0524656 U

(51) Int. Cl.
A24F 47/00 (2006.01)
A61M 15/06 (2006.01)
F22B 1/18 (2006.01)
A61M 11/04 (2006.01)

(52) U.S. Cl.
CPC ......... A24F 47/008 (2013.01); A61M 11/048 (2014.02); A61M 15/06 (2013.01); F22B 1/18 (2013.01); *A61M 2205/3653* (2013.01)

(58) Field of Classification Search
CPC .............................. A24F 47/004; A61M 15/06
See application file for complete search history.

(56) References Cited

U.S. PATENT DOCUMENTS 4,036,224 A * 7/1977 Choporis .......... A61M 16/1075
128/202.21
2002/0100487 A1 * 8/2002 St. Charles ........... A24F 47/004
131/185
2004/0031495 A1 * 2/2004 Steinberg .................. A24F 1/00
131/194
2008/0149118 A1 * 6/2008 Oglesby ............... A61M 11/047
131/194
2008/0257367 A1 * 10/2008 Paterno ................. A24F 47/008
131/328
2008/0302374 A1 * 12/2008 Wengert ................ A24F 47/004
131/178
2010/0043809 A1 * 2/2010 Magnon ................ A24F 47/006
131/178
2010/0083959 A1 * 4/2010 Siller .................... A24F 47/006
128/202.21
2012/0037170 A1 * 2/2012 Wan ......................... A24F 1/32
131/270

FOREIGN PATENT DOCUMENTS

CN WO 2013044538 A1 * 4/2013 ............ A61M 15/06

* cited by examiner

*Primary Examiner* — Cynthia Szewczyk
(74) *Attorney, Agent, or Firm* — Tim Tingkang Xia, Esq.; Locke Lord LLP

(57) ABSTRACT

An electronic cigarette is provided, which comprises an atomizing device and a burning device connected to the atomizing device. The burning device is configured to heat the atomizing device, and thus making the atomizing device to produce smog. The following beneficial effects will be achieved when implementing the present application. In the electronic cigarette, a burning device is used to control the atomizing device to produce smog. As a result, the pollution to the environment resulted from the battery can be avoided, which make the electronic cigarette more friendly to the environment. Besides, the cost of using the electronic cigarette is low.

14 Claims, 7 Drawing Sheets

ELECTRONIC CIGARETTE

CROSS-REFERENCE TO RELATED APPLICATIONS

This non-provisional application claims priorities under 35 U.S.C. §119(a) on Patent Application No. 201320524656.4 filed in P.R. China on Aug. 26, 2013, the entire contents of which are hereby incorporated by reference.

FIELD OF THE APPLICATION

The present application relates to the field of daily electronic products, and more particularly, relates to an electronic cigarette.

BACKGROUND OF THE APPLICATION

The electronic cigarette is mainly used for a user to give up smoking and replace the cigarette. The traditional electronic cigarette always uses a battery to power the atomizing device, and thus making the atomizing device to produce smog for the user to take in. However, the structure with a battery may increase the cost. Besides, the battery is easy to pollute the environment, namely it is not environmentally friendly.

SUMMARY OF THE APPLICATION

The object of the present application is to provide an electronic cigarette, which is at low cost and friendly to the environment, aiming at the drawbacks that the traditional electronic cigarette with a battery is high in cost and not friendly to the environment in the prior art.

The technical schemes to solve the above technical problems are as follows.

In one aspect, an electronic cigarette is provided. It comprises an atomizing device and a burning device connected to the atomizing device, the burning device is configured to heat the atomizing device, and thus making the atomizing device to produce smog.

In one embodiment, the atomizing device comprises a sleeve and a heat conductive rack; the sleeve is mounted on the burning device; the heat conductive rack is mounted at one end of the sleeve, wherein the end of the sleeve is adjacent to the burning device; the burning device can make the atomizing device to produce smog through heating the heat conductive rack.

In the embodiment, the atomizing device further comprises an oil guiding member and an oil storing member, the oil guiding member and the oil storing member are installed inside the sleeve; the oil guiding member abuts against the heat conductive rack and the oil storing member respectively. The oil guiding device is U-shaped; the bending portion of the U-shaped oil guiding member abuts against the heat conductive rack; both ends of the U-shaped oil guiding member abut against the oil storing member respectively.

In the embodiment, the atomizing device further comprises an oil isolating stand that is installed inside the sleeve; the oil isolating stand is located between the oil storing member and the heat conductive rack; the oil guiding member runs across the oil isolating stand and extends out from both ends of the oil isolating stand, so that the two sides of the oil guiding member can abut against the heat conductive rack and the oil storing member respectively.

In the embodiment, the atomizing device further comprises a nozzle component mounted at one end of the sleeve, wherein the end of the sleeve is away from the heat conductive rack. The nozzle component is bent.

In the embodiment, the atomizing device further comprises a sealing member mounted between the nozzle component and the oil storing member.

In the embodiment, the atomizing device further comprises a ventilating pipe mounted along the axis of the oil storing member, and the ventilating pipe is configured to discharge the smog produced by the atomizing device.

In another embodiment, the heat conductive rack comprises a supporting portion, a heat conductive portion and a ventilating portion; the supporting portion is mounted on the sleeve; the heat conductive portion extends from the supporting portion towards the side away from the burning device; the ventilating portion extends from the terminal of the heat conductive portion towards the inner wall that is adjacent to the sleeve; the oil guiding member abuts against the heat conductive portion; the supporting portion, the heat conductive portion and the ventilating portion form an air passage for discharging the smog or gas produced from the burning process in the burning device.

In the embodiment, the heat conductive portion is trumpet-shaped, and the oil guiding member twines around the heat conductive portion.

In the embodiment, a first ventilating hole is provided on the sleeve; the first ventilating hole and the ventilating portion are set oppositely and communicated with each other.

In the aspect, the burning device comprises a case, a gas storing cavity, a flaming valve component and an igniter; the case is connected to the atomizing device; the gas storing cavity is defined inside the case; the flaming valve component is installed in one end of the gas storing cavity, wherein the end of the gas storing cavity is adjacent to the atomizing device; the igniter is mounted in the case; the conductive wire of the igniter is placed at one end of the flaming valve component, wherein the end of the flaming valve component is adjacent to the atomizing device.

In one embodiment, the igniter is a piezo-electric igniter.

In the embodiment, the burning device further comprises a press cap and a prying plate; the press cap is mounted on the case and used to turn on the piezo-electric igniter; one end of the prying plate is located at one side of the press cap, wherein the side of the press cap is adjacent to the piezo-electric igniter; the middle of the plying plate abuts against the piezo electric igniter; the other end of the plying plate abuts against the flaming valve component; when the press cap has been pressed, the plying plate can turn on or turn off the flaming valve component.

In the embodiment, the burning device further comprises a lifting frame installed on the case; the atomizing device is mounted at one side of the lifting frame, wherein the side of the lifting frame is away from the gas storing cavity.

The following beneficial effects will be achieved when implementing the electronic cigarette of the present application. In the electronic cigarette, a burning device is used to control the atomizing device to produce smog. As a result, the pollution to the environment resulted from the battery can be avoided, which make the electronic cigarette more friendly to the environment. Besides, the cost of using the electronic cigarette is low.

BRIEF DESCRIPTION OF THE DRAWINGS

The present application will be further described with reference to the accompanying drawings and embodiments in the following, in the accompanying drawings.

DETAILED DESCRIPTION OF THE PREFERRED EMBODIMENTS

To make the objects, technical schemes and advantages more clearly, the present application may be further described in detail with reference to the accompanying drawings and embodiments.

Figure 1:
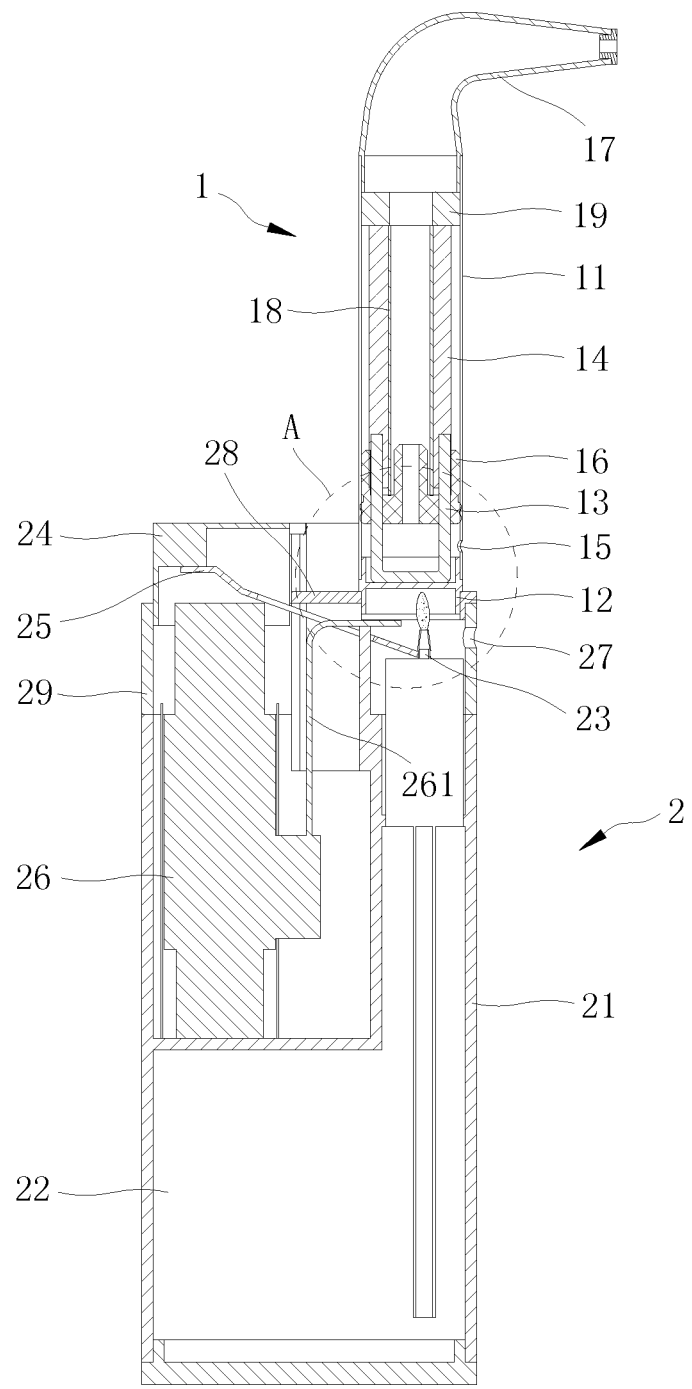
FIG. 1 is a structure diagram of an electronic cigarette in a first preferred embodiment of the present application.
Figure 2:
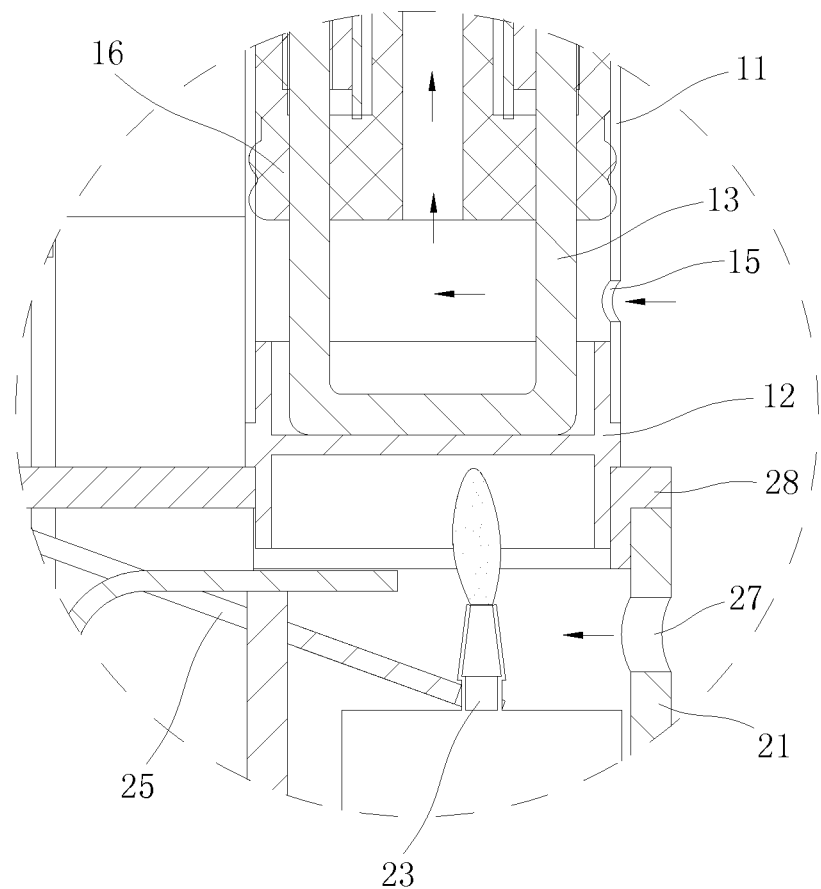
FIG. 2 is an enlarged view of the portion A in FIG. 1.
Figure 3:
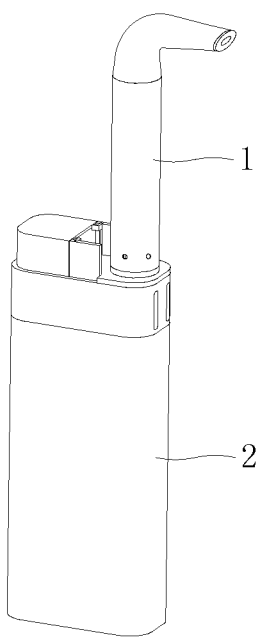
FIG. 3 is a three-dimensional structure diagram of the electronic cigarette shown in FIG. 1.

Referring to FIGS. 1 to 3, a first preferred embodiment of an electronic cigarette is provided. The electronic cigarette comprises an atomizing device 1 and a burning device 2. The atomizing device 1 and burning device 2 are connected to each other. When in work, the burning device 2 can produce fire source to heat the atomizing device 1, and thus making the atomizing device 1 to produce smog for the user to take in.

Figure 4:
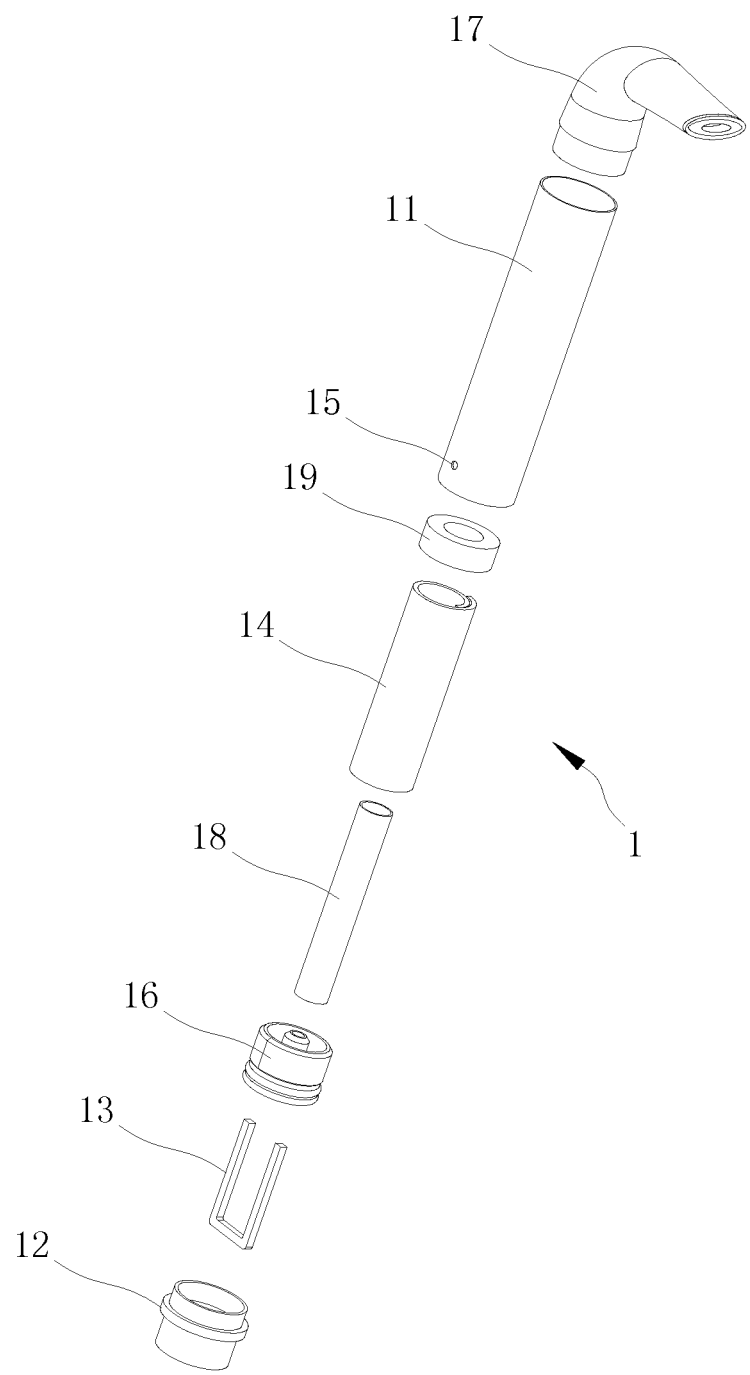
FIG. 4 is an explosive view of the atomizing device in the electronic cigarette shown in FIG. 1.

Specifically, referring to FIGS. 1,2 and 4, the atomizing device 1 comprises a sleeve 11, a heat conductive rack 12, a oil guiding member 13, a oil storing member 14, a first ventilating hole 15, a oil isolating stand 16, a nozzle component 17, a ventilating pipe 18 and a sealing member 19. The sleeve is substantially a hollow cylinder which is mounted on the burning device 2. In this embodiment, the sleeve 11 is fixedly mounted on the burning device 2. In other embodiments, the sleeve 11 can be mounted on the burning device 2 in a detachable way. The heat conductive rack 12 is substantially a cylinder, and its cross section which goes through its axis is substantially I-shaped. The heat conductive rack 12 has good thermal conductive ability and good high temperature resisting ability. The heat conductive rack 12 is mounted at one end of the sleeve 11, wherein the end of the sleeve 11 is adjacent to the burning device 2. The burning device 2 can make the atomizing device 1 to produce smog through heating the heat conductive rack 12. In this embodiment, the outer wall of one end of the heat conductive rack 12 is mounted in the sleeve 11, and the outer wall of the other end of the heat conductive rack 12 is mounted in the burning device 2. One side of the oil guiding member 13 abuts against the heat conductive rack 12, and the other side of the oil guiding member 13 abuts against the oil storing member 14. In this embodiment, the oil guiding member 13 is U-shaped, the bending portion (not labeled) of the U-shaped oil guiding member 13 abuts against the heat conductive rack 12 mutually. and both ends (not labeled) of the U-shaped oil guiding member 13 abut against the oil storing member 14 respectively. The oil storing member 14 is substantially a hollow cylinder which is used to store the tobacco oil. In this embodiment, the oil storing member 14 is a oil storing cotton.

Referring to FIGS. 1,2 and 4, the first ventilating hole 15 is provided on the sleeve 11 located adjacent to the position where the oil guiding member 13 abuts against the heat conductive rack 12 mutually. The first ventilating hole 15 is communicated with the outside and the ventilating pipe 18, and they forms an air passage to enable the gas to flow. The oil isolating stand 16 is substantially a cylinder which is installed inside the sleeve 11. The oil isolating stand 16 abuts against the inner wall of the sleeve 11 and has a good sealing ability. The oil isolating stand 16 is located between the oil storing member 14 and the heat conductive rack 12, which may effectively prevent the tobacco oil in the oil storing member 14 from flowing to the heat conductive rack 12 along the inner wall of the sleeve 11. In this embodiment, the oil guiding member 13 runs across the oil isolating stand 16 and extends out from both ends of the oil isolating stand 16, so that the two sides of the oil guiding member 13 can respectively abut against the heat conductive rack 12 and the oil storing member 14. The nozzle component 17 is bent, which is mounted at one end of the sleeve 11, wherein the end of the sleeve 11 is away from the heat conductive rack 12. In this embodiment, the nozzle component 17 is designed to be a bent structure, which may be convenient for users. The ventilating pipe 18 is a hollow cylinder, which is mounted along the axis of the oil storing member 14 and configured to discharge the smog produced by the atomizing device 1. In this embodiment, the ventilating pipe 18 is a yellow wax pipe. The sealing member 19 is substantially a hollow ring, which is mounted between the nozzle component 17 and the oil storing member 14. The sealing member 19 abuts against the inner wall of the sleeve 11 mutually, which may effectively prevent the user to take in the tobacco oil when smoking.

Figure 5:
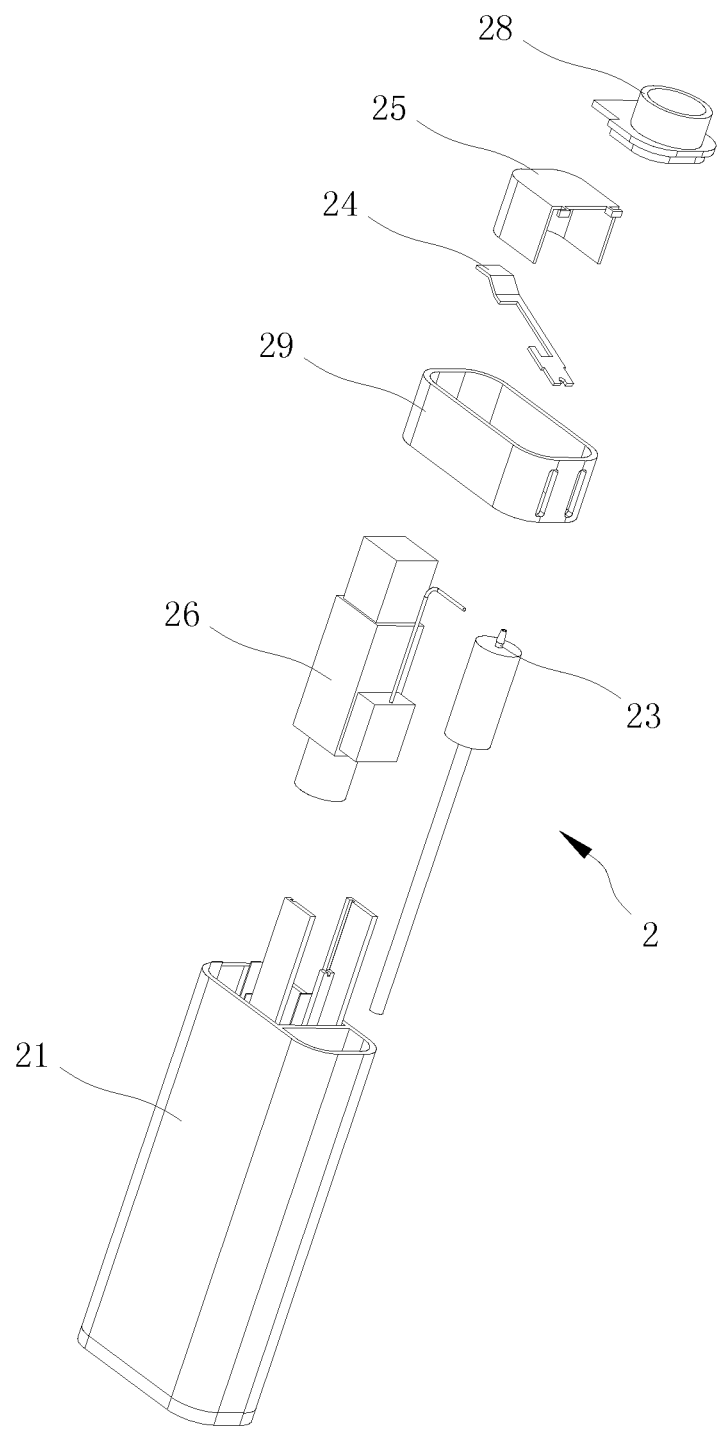
FIG. 5 is an explosive view of the burning device in the electronic cigarette shown in FIG. 1.

Referring to FIGS. 1,2 and 5, the burning device 2 comprises a case 21, a gas storing cavity 22, a flaming valve component 23, a press cap 24, a plying plate 25, an igniter 26, a second ventilating hole 27, a lifting frame 28 and a joint stand 29. The case 21 is substantially a cuboid, and the sleeve 11 is mounted at the edge of one end of the case 21. The gas storing cavity 22 is defined inside the case 21 and it is located at the side that is away from the atomizing device 1. The gas storing cavity 22 is used to store the liquefied gas. The flaming valve component 23 is installed in the gas storing cavity 22 and is located at the end that is adjacent to the atomizing device 1. The flaming valve component 23 is placed opposite to the heat conductive rack 12. And the flaming valve component 23 is configured to turn on or turn off the gas storing cavity 22. The igniter 26 is mounted in the case 21. The conductive wire 261 of the igniter 26 is placed at one end of the flaming valve component 23, wherein the end of the flaming valve component 23 is adjacent to the atomizing device 1. In this embodiment, the igniter 26 is a piezo-electric igniter, which can produce current when being pressed. At this time, a fire source will appear at the flaming valve component 23 when the flaming valve component 23 is turned on. In other embodiments, the igniter 26 may be a flint or the like to enable a fire source to appear at the flaming valve component 23.

Referring to FIGS. 1,2 and 5, the press cap 24 is a hollow block, which is mounted on the case 21 and sheathed on the igniter 26. The press cap 24 is configured to turn on the igniter 26. The plying plate 25 is substantially a plate. One end of the prying plate 25 is located at one side of the press cap 24, wherein the side of the press cap 24 is adjacent to the igniter 26. The middle of the plying plate 25 abut against the piezo-electric igniter. The other end of the plying plate 25 abuts against the flaming valve component 23 mutually. When the press cap 24 has been pressed, the plying plate 25 can turn on or turn off the flaming valve component 23. In this embodiment, the end of the plying plate which abuts the flaming valve component 23 mutually is U-shaped. The U-shaped groove is inserted into the valve opening of the flaming valve component 23 and can turn on or turn off the valve opening. When the press cap 24 has been pressed, the flaming valve component 23 will be turned on and the igniter 26 is triggered to produce current. In the case, a fire source appears from the flaming valve component 23. The second ventilating hole 27 is defined on the case 21 and located adjacent to the flaming valve component 23. The second ventilating hole 27 is communicated with the outside to provide the air demanded in the operation of the burning device 2. The lifting frame 28 is installed on the case 21. The atomizing device 1 is mounted at one side of the lifting frame 28, wherein the side of the lifting frame 28 is away from the gas storing cavity 22, namely the atomizing device 1 is installed on the case 21 via the lifting frame 28. In this embodiment, the lifting frame 28 comprises a fix portion (not labeled) mounted on the case 21 and a insert portion (not labeled) for mounting the sleeve 11. The fix portion is substantially a plate. The insert portion is substantially a hollow cylinder. The atomizing device 1 is mounted in the insert portion. The joint stand 29 is sheathed on one end of the case 21, wherein the end of the case 21 is adjacent to the atomizing device 1. The joint stand 29 and the case 21 are matched in contour. The press cap 24 and the lifting frame 28 are both mounted on the joint stand 29. With the joint stand 29, the assembly for the flaming valve component 23, the press cap 24, the plying plate 25 and the igniter 26 can be more convenient.

In the electronic cigarette, a burning device 2 is used to generate a fire source to control the atomizing device 1 to produce smog. As a result, the pollution to the environment resulted from the battery can be avoided, which make the electronic cigarette more environmentally friendly. Besides, the cost of using the electronic cigarette is low.

Figure 6:
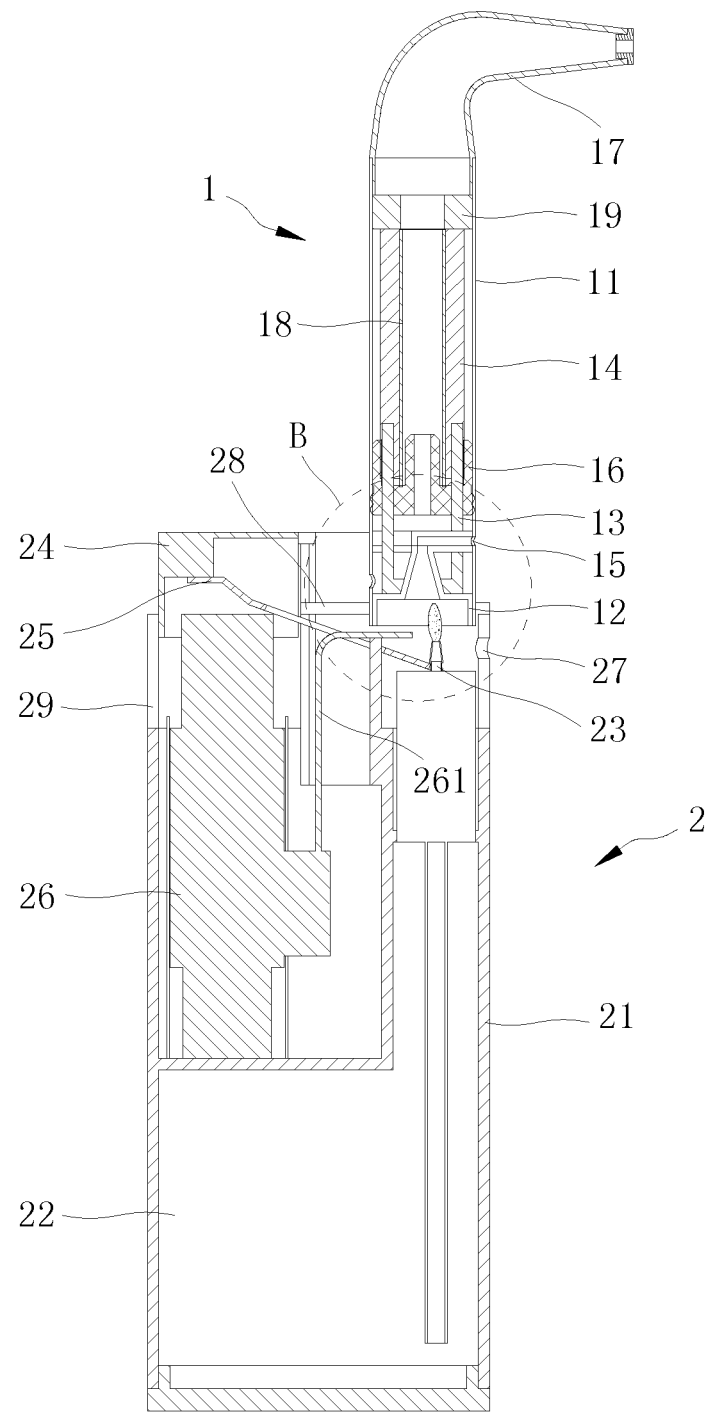
FIG. 6 is a structure diagram of an electronic cigarette in a second preferred embodiment of the present application.
Figure 7:
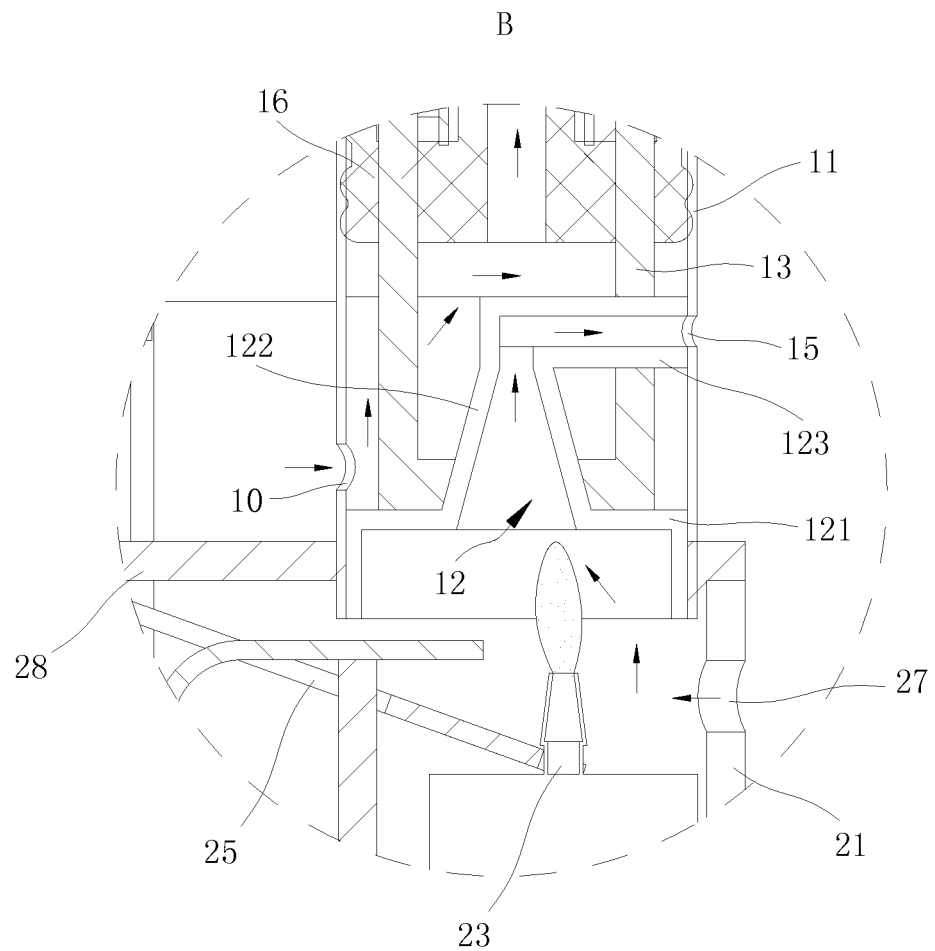
FIG. 7 is an enlarged view of the portion B in FIG. 6.

Referring to FIGS. 6 and 7, a second preferred embodiment of an electronic cigarette is provided. Compared with the first embodiment, the structure of the heat conductive rack 12 and the structure of the sleeve 11 are different in the second embodiment. In the embodiment, the heat conductive rack 12 comprises a supporting portion 121, a heat conductive portion 122 and a ventilating portion 123. The supporting portion 121 is substantially a hollow disk, which is mounted on the sleeve 11 and is located at the end adjacent to the burning device 2. The heat conductive portion 122 is trumpet-shaped, which extends from the supporting portion 121 towards the side away from the burning device 2. The ventilating portion 123 extends from the terminal of the heat conductive portion 122 towards the inner wall that is adjacent to the sleeve 11. The supporting portion 121, the heat conductive portion 122 and the ventilating portion 123 form a air passage for discharging the smog or gas produced from the burning process in the burning device 2. The oil guiding member 13 twines around the heat conductive portion 122. With the structures of the supporting portion 121, the heat conductive portion 122 and the ventilating portion 123, the heat that is accumulated by the heat conductive rack 12 from the burning device 2 can be more intensive, and thus making the oil guiding member 13 to produce smog with a better effect. The first ventilating hole 15 defined on the sleeve 11 is located opposite to the ventilating portion 123. Referring to the arrow in FIG. 7, since the first ventilating hole 15 and the second ventilating hole 27 are both communicated with the outside, an air passage for gas ventilating can be formed among the first ventilating hole 15, the heat conductive rack 12 and the second ventilating hole 27, in order to afford the air demanded in the operation of the burning device 2. A third ventilating hole 10 is also provided in the sleeve 11. The third ventilating hole 10 is communicated with the ventilating pipe 18. The gas flowing direction in the atomizing device 1 is shown in FIG. 7.

While the embodiments of the present application have been described with reference to the drawings, the present application will not be limited to above embodiments that are illustrative but not limitative. It will be understood by those skilled in the art that various changes and equivalents may be substituted in the light of the present application without departing from the scope of the present application, and those various changes and equivalents shall fall into the protection of the application.

What is claimed is:

1. An electronic cigarette, wherein it comprises an atomizing device and a burning device connected to the atomizing device, the burning device is configured to heat the atomizing device, and thus making the atomizing device to produce smog;
   wherein the atomizing device comprising:
   a sleeve mounted on the burning device;
   a heat conductive rack mounted on one end of the sleeve, the end of the sleeve is adjacent to the burning device;
   an oil guiding member; and
   an oil storing member;
   wherein the oil guiding member and the oil storing member are installed inside the sleeve; and the oil guiding member abuts against the heat conductive rack and the oil storing member respectively; and
   wherein the burning device can make the atomizing device to produce smog through heating the heat conductive rack.

2. The electronic cigarette according to claim 1, wherein the oil guiding member is U-shaped; the bending portion of the U-shaped oil guiding member abuts against the heat conductive rack; both ends of the U-shaped oil guiding member abut against the oil storing member respectively.

3. The electronic cigarette according to claim 1, wherein the atomizing device further comprises an oil isolating stand that is installed inside the sleeve; the oil isolating stand is located between the oil storing member and the heat conductive rack; the oil guiding member runs across the oil isolating stand and extends out from both ends of the oil isolating stand, so that the two sides of the oil guiding member can abut the heat conductive rack and the oil storing member respectively.

4. The electronic cigarette according to claim 1, wherein the atomizing device further comprises a nozzle component mounted at one end of the sleeve, wherein the end of the sleeve is away from the heat conductive rack.

5. The electronic cigarette according to claim 4, wherein the nozzle component is bent.

6. The electronic cigarette according to claim 4, wherein the atomizing device further comprises a sealing member mounted between the nozzle component and the oil storing member.

7. The electronic cigarette according to claim 1, wherein the atomizing device further comprises a ventilating pipe mounted along the axis of the oil storing member, and the ventilating pipe is configured to discharge the smog produced by the atomizing device.

8. The electronic cigarette according to claim 1, wherein the heat conductive rack comprises a supporting portion, a heat conductive portion and a ventilating portion; the supporting portion is mounted on the sleeve; the heat conductive portion extends from the supporting portion towards the side away from the burning device; the ventilating portion extends from the terminal of the heat conductive portion towards the inner wall that is adjacent to the sleeve; the oil guiding member abuts against the heat conductive portion; the supporting portion, the heat conductive portion and the ventilating portion form an air passage for discharging the smog or gas produced from the burning process in the burning device.

9. The electronic cigarette according to claim 8, wherein the heat conductive portion is trumpet-shaped, and the oil guiding member twines around the heat conductive portion.

10. The electronic cigarette according to claim 9, wherein a first ventilating hole is provided on the sleeve; the first ventilating hole and the ventilating portion are set oppositely and communicated with each other.

11. The electronic cigarette according to claim 1, wherein the burning device comprises a case, a gas storing cavity, a flaming valve component and an igniter; the case is connected to the atomizing device; the gas storing cavity is defined inside the case; the flaming valve component is installed in one end of the gas storing cavity, wherein the end of the gas storing cavity is adjacent to the atomizing device; the igniter is mounted in the case; conductive wire of the igniter is placed at one end of the flaming valve component, wherein the end of the flaming valve component is adjacent to the atomizing device.

12. The electronic cigarette according to claim 11, wherein the igniter is a piezo-electric igniter.

13. The electronic cigarette according to claim 12, wherein the burning device further comprises a press cap and a prying plate; the press cap is mounted on the case and used to turn on the piezo-electric igniter; one end of the prying plate is located at one side of the press cap, wherein the side of the press cap is adjacent to the piezo-electric igniter; the middle of the plying plate abuts against the piezo-electric igniter; the other end of the plying plate abuts against the flaming valve component; when the press cap has been pressed, the plying plate can turn on or turn off the flaming valve component.

14. The electronic cigarette according to claim 11, wherein the burning device further comprises a lifting frame installed on the case; the atomizing device is mounted at one side of the lifting frame, wherein the side of the lifting frame is away from the gas storing cavity.

* * * * *